United States Patent [19]
Webster et al.

[11] Patent Number: 5,569,668
[45] Date of Patent: Oct. 29, 1996

[54] INDOLE DERIVATIVES WITH ANTIBACTERIAL AND ANTIMYCOTIC PROPERTIES

[76] Inventors: John M. Webster, 5551 Molina Road., North Vancouver, B.C., Canada, V7R 4P3; Jianxiong Li, 117 Buckingham Dr., Port Moody, BC, Canada, V3H 2T4; Genhui Chen, 725 Louis Riel, Simon Fraser University, Burnaby, BC, Canada, V5A 1S6

[21] Appl. No.: 412,455

[22] Filed: Mar. 29, 1995

[51] Int. Cl.$^6$ .......................... A61K 31/40; C07D 209/14
[52] U.S. Cl. ............................ 514/419; 548/504; 548/507
[58] Field of Search ............................ 514/419; 548/504, 548/507

[56] References Cited

U.S. PATENT DOCUMENTS 5,245,046  9/1993  Youngdale et al. ...................... 548/495

FOREIGN PATENT DOCUMENTS 1028812  5/1966  United Kingdom ................... 548/507
94/1247  6/1994  WIPO .................................... 548/507

OTHER PUBLICATIONS

Akhurst, R. J. and N. E. Boemare "A numerical Taxonomic Study of the Genus *Xenorhabdus* (Enterobactereacea) and Proposed Elevation of the Subspecies of *X. nematophilus* to Species " *J. Gen. Microbiol.* vol. 134, 1835–1845 (1988).
American Phytopathological Society. Methods for Evaluating Pesticides for Control of Plant Pathogens. St. Paul, Ma, (1986). Mitchell, D. J. pp. 63–66.
Chen, G., G. B., Dunphy, and J. M., Webster. "Antimycotic Activity of Two *Xenorhabdus* Species and *Photorhabdus luminescens*. Bacteria Associated with the Nematodes *Steinernema* Species and *Heterorhabditis megidis*". *Biol. Control*, vol. 4, 157–161 (1994).
Maxwell et al. "Stability and Activities of Antibiotics Produced during Infection of the Insect *Galleria mellonella* by Two Isolates of *Xenorhabdus nematophilus*" *Appl. Environ. Microbiol.* vol. 60, 715–721 (1994).

McInerney et al. "Biologically Active Metabolites from *Xenorhabdus* spp., Part 1. Dithiolopyrrolone Derivatives with Antibiotic Activity" *J. Nat. Prod.* vol. 54, 774–784 (1991).
McInerney et al. "Biologically Active Metabolites from *Xenorhabdus* spp., Part 2. Benzopyran–1–one Derivatives with Gastroprotective Activity" *J. Nat. Prod.* vol. 54, 785–795 (1991).
National Committee for Clinical Laboratory Standards. "Methods for Dilution of Antimicrobial Susceptibility Tests for Bacteria That Grow Aerobically". Approved standards M–7A2. National Committee for clinical Laboratory Standards, Villaniova, Pa. (1990). pp. 33–69.
Paul et al., "Antibiotics in Microbial Ecology: Isolation and Structure Assignment of Several New antibacterial Compounds from the Insect–Symbiotic Bacteria *Xenorhabdus* spp." J. Chem. Ecol. vol. 7, 589–597 (1981).
Putz et al. "Development and Application of Oligonucleotide Probes for Molecular Indentification of *Xenorhabdus* Species" *Appl. Environ. Microbial.* vol. 56, 181–186 (1990).
Richardson et al., "Identification of an Anthraquinone pigment and a Hydroxystilbene Antibiotic from *Xenorhabdus*" *App. Environ. Microbial.* vol. 54, 1602–1605 (1988).
Vogel, A. I., Vogels Textbook of Practical Organic Chemistry. 5th Ed. Longman, London (1989). pp. 1261–1262.
Caten, C. E. and J. L. Jinks. "Spontaneous Variability of Single Isolates of *Phytophthora infestans*. I. Cultural Variation." *Can. J. Bot.* 46:329(1967).

*Primary Examiner*—Jacqueline Haley

[57] ABSTRACT

The invention is drawn to an antibiotic, NEMATOPHIN, 3-indoleethyl 3'-methyl-2-oxo-pentanamide (+stereoisomer, –stereoisomer and racemic mixture) and its derivatives, 3-indoleethyl 2-oxo-alkanamides, 3-indoleethyl 2-oxo-alkanoates with or without substitute(s) on the indole ring, produced by bacterial symbiont *Xenorhabdus nematophilus* and/or other Xenorhabdus species or synthesized by reaction of tryptamine or substituted tryptamine and 2-oxo-alkanoic acid or its derivative, the additional salts thereof, the pharmaceutical compositions thereof and their use as medicaments, particularly in the treatment of infectious diseases involving microorganisms susceptible to them, including antibiotic-resistant Staphylococcus.

3 Claims, 1 Drawing Sheet

Derivatives of Nematophin

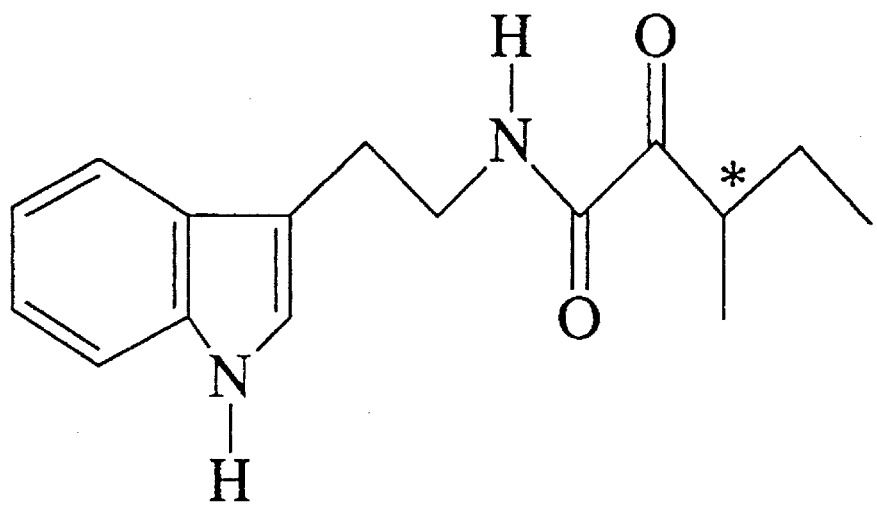
Fig. 1: Nematophin
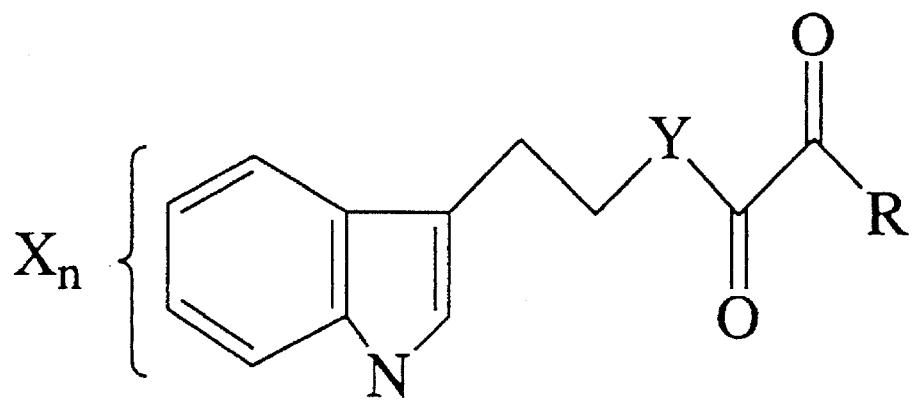
Fig. 2: Derivatives of Nematophin

INDOLE DERIVATIVES WITH ANTIBACTERIAL AND ANTIMYCOTIC PROPERTIES

FIELD OF THE INVENTION

The present invention relates to the novel antibiotic nematophin and its derivatives, which may be obtained by cultivation of Xenorhabdus spp. or by chemical synthesis.

SUMMARY OF THE INVENTION

The present invention provides the novel antibiotics, nematophin and its derivatives having antimicrobial activity, and salts thereof. The present invention also provides methods for the production of nematophin and its derivatives, comprising the step of cultivating the microorganism *X. nematophilus* or the organic synthetic methods. The present invention further provides novel antimicrobial compositions comprising nematophin and its derivatives or their salts thereof, and methods of using the inventive compounds as antibacterial and antimycotic agents.

BRIEF DESCRIPTION OF THE DRAWING

The following FIG. 1 shows the structural formula of nematophin, 3-indoleethyl 3-methyl-2-oxo-pentanamide.

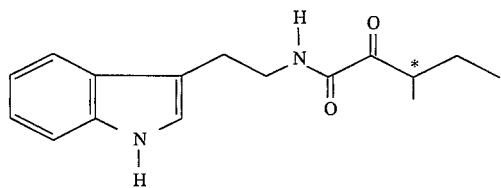

FIG. 1

The following FIG. 2 shows the structural formula of a novel group of compounds, related to nematophin, where X=chloro, fluoro, methyl, methoxyl, nitro, alkyl, aryl; n=1–6; Y=NH, O, S; R=straight chain or branched, or substituted alkyl or aryl group.

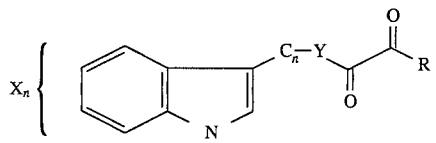

FIG. 2

BACKGROUND

Protection of humans, agricultural crops, stored foods, gardens, ornamental plants, trees and wood products, and animals from bacterial and fungal diseases is extremely important. Unfortunately, bacteria and fungi continue to be problematic pathogens for humans because of the increasing occurrence of strains which are resistant to commonly used antibiotics. Such resistant strains lead to a constant need for new antibacterial and antifungal.

Although there are a limited number of publications on Xenorhabdus and Photorhabdus, it has been recognized that active, antibacterial and antifungal substances are produced by Xenorhabdus species and Photorhabdus species. Some of these specific compounds have been isolated, identified and their structures elucidated (Li et al., "Antimicrobial metabolites from a bacterial symbiont" *J. Nat. Prod.* Vol. 58, 1081–1086 (1995) Paul et al., "Antibiotics in Microbial Ecology: Isolation and Structure Assignment of Several New Antibacterial Compounds from the Insect-Symbiotic Bacteria Xenorhabdus spp." *J. Chem. Ecol.* Vol. 7, pp. 589–597 (1981); Richardson et al., "Identification of an Anthraquinone Pigment and a Hydroxystilbene Antibiotic from Xenorhabdus [Photorhabdus]" *App. Environ. Microbiol.* Vol. 54, pp. 1602–1605 (1988);. McInerney et al. "Biologically Active Metabolites from Xenorhabdus spp., Part 1. Dithiolopyrrolone Derivatives with Antibiotic Activity" *J. Nat. Prod.* Vol. 54, pp. 774–784 (1991a); McInerney et al. "Biologically Active Metabolites from Xenorhabdus spp., Part 2. Benzopyran-1-one Derivatives with Gastroprotective Activity" *J. Nat. Prod.* Vol. 54, pp. 785–795 (1991b). Recently the cell free culture broths of Xenorhabdus species and *P. luminescens*, bacterial symbionts carried by nematodes of the genus Steinernema, and Heterorhabditis were found to be active against many fungi of agricultural and medicinal importance Chen et al., Antifungal activity of two Xenorhabdus species and *P. luminescens*, bacteria associated with the nematodes Steinernema species and *Heterorhabditis megidis*. *Biological Control*. Vol. 4, 157–162(1994)). However, 3-indoleethyl 2'-oxo-alkanamides and 3-indoleethyl 2'-oxo-alkanoates with or without substitute(s) on indole ring, a novel group of antibiotics and the importance of these specific purified metabolites as extremely potent antibacterial and antifungal agents have heretofore been undiscovered until now, that are the subjects of this invention. Prior art references have not shown use of these specific compounds or any operable aspects as antibacterial and antifungal agents.

DESCRIPTION OF THE INVENTION

The microorganisms

*X. nematophilus* and its nematode symbiont *Steinernema feltiae* used in this study were collected from soil in British Columbia, Canada and maintained in culture in this laboratory (Maxwell et al. 1994). Briefly, last instar larvae of the greater wax moth, *Galleria mellonella*, were infected with infective juvenile (IJ) nematodes, carrying the *X. nematophilus* BC1 strain, at a rate of 25 IJs/larvae. After 24 to 48 h the dead insect larvae were surface disinfected by dipping them into 95% EtOH and igniting them. The cadavers were aseptically dissected, haemolymph was streaked onto an NBTA medium (nutrient agar supplemented with 0.025 grams of bromothymol blue and 0.04 gram of 2,3,5-triphenyltetrazolium chloride per liter) and incubated in the dark at room temperature. The resulting primary form of *X. nematophilus* was maintained and subcultured at 14 d intervals. Other sources and depositories of Xenorhabdus species and strains are noted in Akhurst and Boemare "A numerical taxonomic study of the genus Xenorhabdus (Enterobactereacea) and proposed elevation of the subspecies of *X. nematophilus* to species" *J. Gen. Microbiol.* Vol 134, pp. 1835–1845 (1988). Putz et al. "Development and application of oligonucleotide probes for molecular identification of Xenorhabdus species" *Appl. Environ. Microbiol.* Vol. 56, pp. 181186 (1990) notes additional sources and depositories, including the American Type Culture Collection, Rockville, Md. Candidate bacterial and fungal pathogens used in bioassays are readily available from many sources, including the American Type Culture Collection, Rockville, Md. For consistency, 14% sucrose lyophilized powder of bacteria stored at −20° C. was frequently used as starting material for cultures.

Preparation of nematophin and its derivatives

Cultivation of the microorganism *X. nematophilus* BC1 strain yields the novel antimicrobial substance nematophin (+stereoisomer). Nematophin may be formed as a metabolite thereof.

To prepare nematophin, *X. nematophilus* BC1 strain may be cultivated (fermented), for example, at about 25° C. under submerged aerobic conditions in an aqueous nutrient medium containing assimilable carbon (carbohydrate) and nitrogen sources until antibiotic activity due to nematophin is imparted to the medium. The fermentation may be carried out for a time period such as approximately 48 to 96 hours, at the end of which time the antibiotic nematophin has been formed, and may be isolated from the fermentation medium and purified.

After the fermentation has been completed, the fermented broth may be filtered or centrifuged and the pH of the filtrate adjusted to about 7.0 by the addition of hydrochloric acid or kept as it was. The filtrate may then be extracted with a water immiscible organic solvent, for example, with ethyl acetate or chloroform. The combined organic layers (e.g. pooled ethyl acetate or chloroform extracts) may be concentrated in vacuum (e.g. at about 30° C.) to an oily residue ("syrup"). The oil may be mixed with a small amount of organic solvent and chromatographed on a silica gel column (EM Science, Darmstadt, Germany). After introduction of the sample, chloroform or other organic solvent may be applied to elute the bioactive fraction out.

The relative simplicity of the organic molecules of the present instance lend themselves to organic synthetic methods, in addition to microbial production methods. Such standard synthetic processes are described in many parts of the chemical literature (Vogel, 1989) and provide a practical way for large scale production. The reaction of tryptamine and 2'-oxo-3'-methylbutanoic chloride, or acid, or anhydride yields nematophin, while the reaction of substituted tryptamine and 2'-oxo-alkanoic acid or its derivative gives the amide derivatives of nematophin, 3-indoleethyl 2'-oxo-alkanamides, and the reaction of substituted tryptol and 2'-oxo-alkanoic acid or its derivative gives the ester derivatives of nematophin, 3-indoleethyl 2'-oxo-alkanoates.

The Antibiotic and Use Thereof

Nematophin and its derivatives possess antibacterial and antimycotic properties, and have been found to have the characteristics shown in the Figures and in Examples herein.

The compounds of the present invention include nematophin and its derivatives, and salts thereof. The term "salts", as used herein, may be formed with inorganic and/or organic acids.

It is preferred that the inventive compounds have a degree of purity such that they are suitable for use as antibiotic agents. A particularly preferred embodiment of the instant invention provides nematophin or a derivative, or a salt thereof in a substantially pure state. The substantially pure compounds are preferably employed in the compositions and methods described following.

The inventive compounds are useful as antimicrobial agents, useful in inhibiting the growth of microorganisms, particularly as an antibiotic drug, useful in treating bacterial infection caused by antibiotic resistant bacteria such as gram positive bacteria, for example, bacteria of the genera Bacillus and Staphylococcus. Inhibition of the growth of a bacterium may be achieved by contacting the bacterium with a compound of the present invention in an amount effective therefor.

Thus, the compounds of the present invention may be employed in utilities suitable for antibacterial and antimycotic agents.

The inventive compounds may, for example, be used in treating a host infected with a bacterium and fungus, comprising the step of administering to the host nematophin or a physiologically tolerated salt thereof in an amount effective for the treatment. Treatment of such infections according to the instant invention includes both mitigation as well as elimination thereof.

Hosts treatable according to the method of the present invention include plants and animals, particularly mammals such as dogs, cats and other domestic animals and, especially, humans. The dosage form and mode of administration, as well as the dosage amount, may be selected by the skilled artisan. The dosage amount will vary with the severity of the infection, and with the size and species of the host. Exemplary daily dosages for an adult human are those within the range of from about 2.5 mg to about 2,000 mg/day. Administration to a mammalian host, may, for example, be oral, parenteral, or topical. Administration to a plant host may be accomplished, for example, by application to seed, foliage or other plant part, or to the soil.

Compositions are also provided by the present invention which comprise nematophin or a physiologically tolerated salt thereof in an amount effective for the treatment of infection by a microorganism, and a physiologically tolerated vehicle or diluent. The term "physiologically tolerated" is equivalent to the term "pharmaceutically acceptable" when used in reference to the treatment of a mammalian host. The appropriate solid or liquid vehicle or diluent may be selected, and the compositions prepared, by methods known to the skilled artisan. Treatment of simultaneous infections by more than one bacterium is, or course, contemplated.

The inventive compounds may be employed also as antibacterial and antimycotic agents useful in inhibiting the growth of microorganisms present on a surface or in a medium outside a living host. The present invention therefore provides a method for inhibiting the growth of at least one microorganism present on a surface or in a medium, comprising the step of contacting the surface or medium with nematophin or a derivative, or a salt thereof in an amount effective for the inhibition. Thus, the inventive compounds may be employed, for example, as disinfectants for a variety of solid and liquid media susceptible to microbial growth. Suitable amounts of the inventive compounds may be determined by methods known to the skilled artisan. Compositions comprising nematophin or a salt thereof in an amount effective for inhibiting the growth of at least one bacterium, and a vehicle or diluent, are also provided by the present invention.

For agricultural application, the bactericidal and fungicidal compositions may be formed using one of the active ingredients in an inert carrier. If formulated as a solid, the ingredients may be mixed with typical carriers such as Fuller's earth, kaolin clays, silicas or other wettable inorganic diluents. Free-flowing dust formulations may also be utilized by combining the dry active ingredient with finely divided solids such as talc, kieselguhr, pyrophyllite, clays, diatomaceous earth and the like.

The powders may also be applied as a suspension or solution, depending on the solubility in the liquid carrier. Pressurized sprays, typically aerosols with the active ingredient dispersed in a low boiling dispersant solvent carrier, may be used. Percentages of weight may vary according to the manner in which the composition is to be applied, and formulation used. In general, the active ingredient will comprise 0.005% to 95% of the active ingredient by weight in the bactericidal and fungicidal composition. The bactericidal and fungicidal composition may be applied with other ingredients, including growth regulators, insecticides, fertilizers, and the like Formulation of the active ingredients to assist applicability, ease handling, maintain chemical stability and increase effectiveness may require addition of various materials. Solvents may be chosen on the basis of affecting the volubility of the active ingredient, fire hazard and flash point, emulsifiability, specific gravity and economic considerations. Adjuvants may be added to enhance the active ingredients, and can include suffactants which are anionic, cationic or nonionic. Stabilizers and antifreeze compounds will prolong storage. Additionally, synergists, stickers, spreaders and deodorant compounds can be added to improve the handling characteristics of the commercial formulation. Alternatively, the active ingredient can be combined with an inert carrier, such as calcium carbonate, and formed into a pill or other consumable delivery device, including controlled release devices intended to deliver metered doses of the active ingredient.

The following examples are provided to further illustrate the invention, and are not intended to in any way limit the scope of the instant claims.

EXAMPLE 1

Preparation of nematophin

A. Isolation of the nematophin from the BC1 strain of *X. nematophilus*

Cultures were shaken at 120 rpm on an Eberbach gyrorotary shaker for 24 h at 25° C. Bacterial fermentation was initiated by adding 100 ml of this bacterial culture to 900 ml of tryptic soy broth (TSB) in a 2,000 ml flask. The flask was incubated in the dark at 25° C. on a gyrorotary shaker. After 96 h, the culture was immediately centrifuged (12,000 g, 20 minutes, 4° C.) to separate the bacterial cells. The cell-free broth (4 l) was then extracted with ethyl acetate 4 times. The combined extracts were dried with anhydrous sodium sulfate and then filtered through filter paper. The filtrate was concentrated on a rotary evaporator below 30° C. under vacuum to yield a brown oil. approximately 2.1 g of the oil was obtained. The crude extracts were then loaded onto a silica gel (200 g silica gel 60, 40 cm×5 cm, EM Science, Darmstadt, Germany) chromatographic column. The bioactive component (NID)(nematophin, +stereoisomer) was eluted out with 100% chloroform. B. Identification of the active component (NID) from BC1 strain of *X. nematophilus*

NMR spectra were recorded on a Bruker WM400 spectrometer in CDCl3, using residual CHCl3 (~7.25) as internal standard. Low resolution mass spectra were obtained on a Hewlett-Packard 5985B GC/MS system operating at 70 eV using a direct probe. High resolution MS spectra were recorded on a Kratos MS80 instrument. IR spectra were recorded as neat film on NaCl using a Perkin-Elmer 599B spectrometer. (Abbreviations used as follows: EI=Electron Impact, $M^+$=Molecular Ion, t=triplet, J=coupling constant, Hz=Hertz, d=doublet, m=multiplet, sext=sextet, dd=doublet doublet, q=quartet, bs=broad singlet, hept=heptet).

NID: $[a]^{25}_D$=+1.0 (c 0.58, CHCl$_3$); EIMS: 273($M^+$+1,24), 272($M^+$, 24), 144(30), 143(89), 131(11), 130(100), 115(6), 103(5), 77(7), 57(8); HRMS: 272.1528 (Calc. for $C_{16}H_{21}N_2O_2$: 272.1525, 22), 143.0727 (Calc. for $C_{10}H_9N$: 143.0735, 100), and 130.0654 (Calc. for $C_9H_8N$: 130.0657, 95); IR(KBr): 3369, 2969, 2933, 2874, 1683, 1619, 1533, 1458, 1380, 1339, 1227, 1168, 1099, 138 cm$^{-1}$; $^1$HNMR (CDCl$_3$) δ: 8.03 (1H, bs,—NH), 7.61 (1H, dd, J=7.9 Hz, J=0.6 Hz), 7.38 (1H, d, J=8.2 Hz), 7.22 (1H, td, J=8.1 Hz, 1.2 Hz), 7.13(1H, td, J=7.9 Hz, J=1.0 Hz) 7.05(2H, bd, J=2.4 Hz), 3.64(2H, q, J=6.8 Hz, CH$_2$), 3.49(1H, sext, J=6.7 Hz, CH), 3.02(2H, t, J=6.9 Hz, CH$_2$), 1.70 (1H, m), 1.39 (1H, m), 1.08(3H, d, J=6.7 Hz, CH$_3$), 0.33(3H, t, J=7.4 Hz); $^{13}$CNMR (CDCl$_3$) δ: 202.4(s, CO), 160.1(s, CONH—), 136.5(s), 127.2(s), 122.3(d), 122.0(d), 119.6(d), 118.7(d), 112.6(s), 111.3(d), 40.4(d, CH), 39.6(t, CH$_2$), 25.5(t, CH$_2$), 25.2(t, CH$_2$), 15.2(q, CH$_3$), 11.5(q, CH$_3$).

C. Synthesis of racemic 3-indoleethyl(3'-methyl-2'-oxo-)pentanamide (SID) (nematophin, racemic mixture).

Sodium 3-methyl-2-oxopentanoate (Aldrich chemical company, Milwaukee, Wis., U.S.A.) was treated with 10% HCl. The acidic solution was extracted with ethyl ether 3 times. The combined ether extracts were then washed with saturated NaCl solution twice, dried over anhydrous Na$_2$SO$_4$ and concentrated under vacuum under 25° C. Thionyl chloride was then added at room temperature to 3-methyl-2-oxopentanoic acid, obtained from above process, under stirring. After stirring for 2 h at about 50° C., the excess of thionyl chloride was evaporated. The solution of tryptamine (Aldrich) in pyridine in excess was added to this crude 3-methyl-2-oxopentanoyl chloride at 0° C. After the reaction was continued under stirring at room temperature for over 2 h, it was quenched with water. The reaction mixture was then extracted with ether 3 times. The combined ether extracts were then washed with saturated NH$_4$Cl$_3$ times, 5% NaOH twice, water twice, saturated NaCl twice, dried over anhydrous Na$_2$SO$_4$ and concentrated under vacuum under 30° C. The crude product was then subjected to silica gel chromatography with ethyl acetate: hexane (1:2) as eluent to yield racemic 3-indoleethyl(3'-methyl-2'-oxo)pentanamide (SID) which had the same R$_f$ values as those of NID on thin layer chromatographic plates developed with different solvents.

The MS, IR, and $^1$HMNR spectra of the product SID were identical to those of the isolated compound NID.

EXAMPLE 2

Nematophin as an antibiotic

The following experiments were conducted, demonstrating the antibiotic properties of nematophin.

To determine minimum inhibitory concentration (MIC) of the nematophin, the standard procedures (The National Committee for Clinical Laboratory Standards and Motheds for Evaluating Pesticides for Control of Plant Pathogens of the Ammerican Pytopathological Society) for testing antibiotics was followed. Briefly, test chemicals were dissolved in dimethyl sulphoxide (DMSO), filter sterilized and diluted into TSB or potato dextrose broth (PDB) or distilled water resulting a final DMSO concentration <0.4% (v/v) at a chemical stock concentration of 1,000 µg/ml. The active compounds were serially diluted by twofold {or mixed with equal amount of media/agar) to produce culture media containing the compound from 100 µg/ml to 0.1 µg/ml (i.e. 100, 50, 25, 12.5, 6.3, 3.2, 1.6, 0.8, 0.4, 0.2, 0.1) for the determination of MICs. Test bacteria were grown on nutrient agar for 24 h (36° C.), then were scraped from the plate by flooding the plate with 0.8% saline and diluted with the saline to make inocula (containing 2.5–2.8×10⁷ CFU/ml). *B. cinerea* was grown on potato dextrose agar for 7 d (25° C.) before the conidia were harvested by flooding the plate with sterile, distilled water and diluted to make the final inocula(2.5–3.0×10⁶ conidia/ml). The inoculated test media were incubated at 35° C. (*B. cinerea* 24° C.) and the MICs were visually determined after 24 h incubation (2 d for *B. cinerea*). The MIC was defined as the lowest chemical concentration which prevents the growth of the test organism at the above conditions. The tests on *Phytophthora infestans* were done on rye agar (Caten & Jinks, 1967). Chemicals were diluted with distilled water, mixed with equal amount of agar, mycelium plug (0.5 cm in diameter) were placed in the center of each plate, incubated at room temperature, MICs determined 4 d after incubation.

RESULTS: It was found that similar results were obtained from both liquid and agar culture methods. Table 1 shows the MICs determined for the compounds against each bacterial organism. In conclusion, it is shown that 3-indoleethyl 2'-oxo-pentanoate, isolated from Xenorhabdus and racemic mixture synthesized chemically show potent properties, in particularly against antibiotic resistant Staphylococcus.

TABLE 1

Minimum Inhibitory Concentrations (MIC) of nematophin, isolated from *Xenorhabdus nematophilus* or synthesized, on candidate microbial pathogens.

| Organisms | MICs(µg/ml) | |
|---|---|---|
| | NID | SID |
| Bacillus subtilis | 12 | 12 |
| Botrytis cinerea | 12 | 12 |
| Escherichia coli ATCC25922 | >100 | >100 |
| Phytophthora infestans | | 2.5 |
| Staphylococcus aureus ATCC29213 | 0.7 | 1.5 |
| S. aureus 0012* | 0.7 | 1.5 |
| S. aureus 0017* | 0.7 | 1.5 |

*clinical isolates of multi-antibiotic-resistant isolates, provided by S. Farmer of the Canadian Bacterial Diseases Network, Vancouver, British Columbia, Canada.

EXAMPLE 3

Preparation of the derivatives of nematophin

A. Synthesis of 3-indoleethyl(2'-oxo)propanamide.

Thionyl chloride was added to 2-oxopropanoic acid (Aldrich chemical company, Milwaukee, Wis., U.S.A.) under stirring at room temperature. After stirring for 2 h at about 50° C., the excess of thionyl chloride was evaporated. The solution of tryptamine (Aldrich) in pyridine in excess was added to this crude 2-oxopropanoyl chloride at 0° C. After the reaction was continued under stirring at room temperature for over 2 h, it was quenched with water. The reaction mixture was then extracted with ether 3 times. The combined ether extracts were then washed with saturated $NH_4Cl_3$ times, 5% NaOH twice, water twice, saturated NaCl twice, dried over anhydrous $Na_2SO_4$ and concentrated under vacuum under 30° C. The crude product was then subjected to silica gel chromatography with ethyl acetate: hexane (1:1) as eluent to yield racemic 3-indoleethyl(2'-oxo)propanamide (PAMIDE).

PAMIDE: EIMS: 230(M⁺, 25), 144(15), 143(51), 131(11), 130(100), 115(5), 103(5), 77(8); ¹HMNR (CDCl₃) δ: 8.03 (1H, bs,—NH), 7.60 (IH, dd, J=7.9 Hz, J=0.6 Hz), 7.38 (1H, d, J=8.2 Hz), 7.22 (1H, td, J=8.1 Hz, 1.2 Hz), 7.13(1H, td, J=7.9 Hz, 1.0 Hz) 7.05(2H, bd, J=2.4 Hz), 3.64(2H, q, J=6.8 Hz, CH₂), 3.02(2H, t, J=6.9 Hz, CH₂), 2.46(s, CH₃).

B. Synthesis of other 3-indoleethyl(2'-oxo)alkanamides.

The same process was used in the synthesis of 3-indoleethyl(2'-oxo)butanamide (BAMIDE). 3-indoleethyl(3'-methyl-2'-oxo)propanamide (MAMIDE).

BAMIDE: EIMS: 244(M⁺, 24), 144(21), 143(62), 131(11), 130(100); ¹HMNR (CDCl₃) δ: 8.03 (1H, bs,—NH), 7.61 (IH, dd, J=7.9 Hz, J=0.6 Hz), 7.38 (1H, d, J=8.2 Hz), 7.22 (1H, td, J=8.1 Hz, 1.2 Hz), 7.13(1H, td, J=7.9 Hz, J=1.0 Hz) 7.05(2H, bd, J=2.4 Hz), 3.64(2H, q, J=6.8 Hz, CH₂), 3.02(2H, t, J=6.9 Hz, CH₂), 2.94(2H, q, J=7.2 Hz, CH₂), 1.08(3H, t, J=7.2 Hz, CH₃).

MAMIDE: ¹HMNR (CDCl₃) δ: 8.03 (1H, bs,—NH), 7.61 (IH, dd, J=7.9 Hz, J=0.6 Hz), 7.38 (1H, d, J=8.2 Hz), 7.22 (1H, td, J=8.1 Hz, 1.2 Hz), 7.13(1H, td, J=7.9 Hz, J=1.0 Hz) 7.05(2H, bd, J=2.4 Hz), 3.63(2H, q, J=6.6 Hz, CH₂), 3.62(1H, sext, J=6.9, CH), 3.02(2H, t, J=6.6 Hz, CH₂), 1.11(6H, d, J=6.9 Hz, CH₃).

C. Synthesis of substituted 3-indoleethyl(3'-methyl-2'-oxo-)pentanamides.

The same process as that discussed above was used in the synthesis of 5-methyl-3-indoleethyl(2'-oxo)pentanamide (5-MeIN), 5-methoxyl-3-indoleethyl(2'-oxo)pentanamide (5-MeOIN) and 6-fluoro-3-indoleethyl(2'-oxo)pentanamide (6-FIN)) except that 5-methyl-tryptamine and 6-fluoro-tryptamine were used respectively instead of tryptamine.

5-MeIN: ¹HMNR (CDCl₃) δ: 7.91 (1H, bs,—NH), 7.37 (IH, q, J=0.8 Hz), 7.26 (1H, d, J=8.2 Hz), 7.03 (2H, m), 3.63(2H, q, J=6.8 Hz, CH₂), 3.49(1H, sext, J=6.7 Hz, CH), 2.99(2H, t, J=6.9 Hz, CH₂), 2.46(3H, s, CH₃), 1.72 (1H, m), 1.39 (1H, m), 1.08(3H, d, J=6.7 Hz, CH₃), 0.88(3H, t, J=7.4 Hz).

5-MeOIN: ¹HMNR (CDCl₃) δ: 7.92 (1H, bs,—NH), 7.27 (IH, dd, J=8.9 Hz, J=0.5 Hz), 7.02 (2H, m), 6.87(1H, dd, J=8.1 Hz, 1.2 Hz), 3.86(3H, s, OCH₃), 3.63(2H, q, J=6.8 Hz, CH₂), 3.49(1H, sext, J=6.7 Hz, CH), 2.99(2H, t, J=6.9 Hz, CH₂), 1.70 (1H, m), 1.39 (1H, m), 1.08(3H, d, J=6.7 Hz, CH₃), 0.88(3H, t, J=7.4 Hz.

6-FIN: ¹HMNR (CDCl₃) δ: 8.03 (1H, bs,—NH), 7.50 (IH, dd, J=8.7 Hz, 5.3 Hz), 7.05 (1H, dd, J=9.6, 2.3 Hz), 7.02 (1H, d, J=2.2 Hz), 6.90(1H, td, J=9.1 Hz, J=2.3 Hz), 3.62(2H, q, J=6.8 Hz, CH₂), 3.49(1H, sext, J=6.7 Hz, CH), 3.00(2H, t, J=6.9 Hz, CH₂), 1.70 (1H, m), 1.39 (1H, m), 1.08(3H, d, J=6.7 Hz, CH₃), 0.88(3H, t, J=7.4 Hz).

D. Synthesis of 3-indoleethyl(3'-methyl-2'-oxo)pentanoate (OIN).

The same process as that for SIN was used in the synthesis of 3-indoleethyl(3'-methyl-2'-oxo)pentanoate except that tryptol was used instead of tryptamine.

OIN: EIMS: 237(M⁺, 0.6), 245(5), 144(19), 143(100), 131(6), 130(64), 115(7), 103(5), 77(7); ¹HMNR (CDCl₃) δ: 7.99 (1H, bs,—NH), 7.65 (IH, dd, J=7.8 Hz, J=0.6 Hz), 7.36 (1H, dd, J=8.0, 0.8 Hz), 7.19 (1H, td, J=8.1 Hz, 1.1 Hz), 7.15(1H, td, J=8.1 Hz, J=1.1 Hz) 7.05(2H, bd, J=2.4 Hz), 4.36(2H, t, J=7.2 Hz, CH₂), 3.11(2H, t, J=6.9 Hz, CH₂), 2.37 (1H, sext, J=6.9)1.66 (1H, m), 1.46 (1H, m), 1.13(3H, d, J=6.7 Hz, CH₃), 0.88(3H, t, J=7.4 Hz).

EXAMPLE 4

The derivatives of nematophin as antibiotics

Similar bioassays as those discribed for nematophin were conducted, demonstrating the antibiotic properties of the derivatives of nematophin.

TABLE 2

Minimum Inhibitory Concentrations (MIC) of the drivatives of nematophin on candidate bacterial pathogens.

| Chemicals | MICs(μg/ml) *Staphylococus aureus* ATCC29213 |
|---|---|
| PAMIDE | 100 |
| BAMIDE | 100 |
| MAMIDE | 3 |
| 5-MeOIN | 3 |
| 5-MeIN | 3 |
| 6-FIN | 0.7 |
| OIN | 25 |

While our above description contains many specificities, these should not be construed as limitations on the scope of the invention, but rather as examples of preferred embodiments. Accordingly, the scope of the invention should not be determined by the embodiments presented, but by the appended claims and their legal equivalents.

What is claimed is:

1. The compound, 3-indoleethyl 3-methyl-2-oxo-pentanamide, named as nematophin, which has the structure shown below in Formula 1

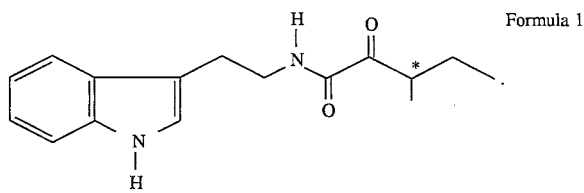

2. A compound of the structural formula 2, related to nematophin, where X=chloro, fluoro, methyl, methoxyl, nitro, alkyl, aryl; n=1–6; Y=NH, O, S; R=straight chain or branched, or substituted alkyl or aryl group

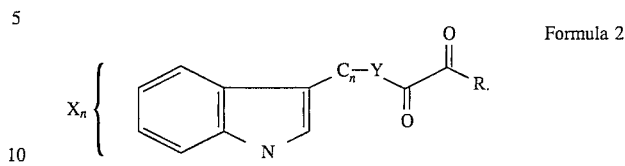

3. A composition for combating bacteria or fungi, comprising a carrier and an effective antifungal or antibacterial amount of a compound of the structure shown below in Formula 1 and Formula 2, its stereoisomer, enantiomeric mixture; where X=chloro, fluoro, methyl, methoxyl, nitro, alkyl, aryl; n=1–6; Y=NH, O, S; R=straight chain or branched, or substituted alkyl or aryl group

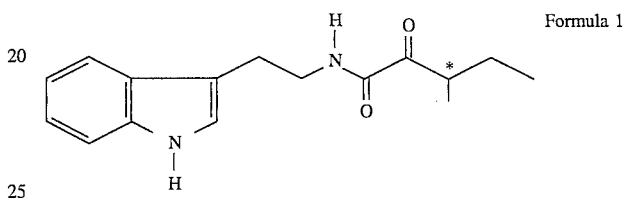

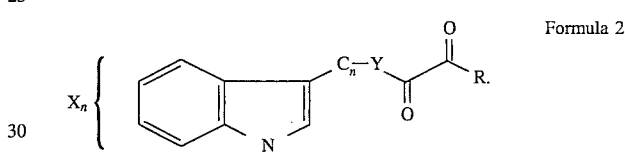

* * * * *